(12) United States Patent
Plank et al.

(10) Patent No.: US 8,382,472 B2
(45) Date of Patent: Feb. 26, 2013

(54) LIGHT CURING DEVICE

(75) Inventors: Wolfgang Plank, Rankweil (AT); Bruno Senn, Buchs (CH)

(73) Assignee: Ivoclar Vivadent AG, Schaan (LI)

(*) Notice: Subject to any disclaimer, the term of this patent is extended or adjusted under 35 U.S.C. 154(b) by 387 days.

(21) Appl. No.: 12/077,721

(22) Filed: Mar. 20, 2008

(65) Prior Publication Data

US 2008/0233533 A1    Sep. 25, 2008

Related U.S. Application Data

(60) Provisional application No. 60/931,579, filed on May 14, 1007.

(30) Foreign Application Priority Data

Mar. 20, 2007    (DE) .................. 10 2007 013 424

(51) Int. Cl.
    *A61C 3/00* (2006.01)
(52) U.S. Cl. .......... 433/29; 362/120; 362/202; 362/572
(58) Field of Classification Search .............. 433/29, 433/30; 600/179; 606/17–19; 362/572–575, 362/577–580, 109, 118–120, 187, 202, 188, 362/277, 280–281, 319
    See application file for complete search history.

(56) References Cited

U.S. PATENT DOCUMENTS

| | | | |
|---|---|---|---|
| 5,471,129 A | 11/1995 | Mann | |
| 5,509,917 A * | 4/1996 | Cecchetti et al. | 606/15 |
| 5,616,141 A * | 4/1997 | Cipolla | 606/15 |
| 5,738,678 A * | 4/1998 | Patel | 606/10 |
| 5,928,220 A * | 7/1999 | Shimoji | 606/2 |
| 6,099,520 A * | 8/2000 | Shimoji | 606/2 |
| 6,102,696 A | 8/2000 | Osterwalder | |
| 6,161,937 A * | 12/2000 | Rosenstatter | 362/109 |
| 6,638,216 B1 * | 10/2003 | Durell | 600/173 |
| 6,741,410 B2 | 5/2004 | Plank | |
| 7,099,732 B2 * | 8/2006 | Geng | 700/117 |
| 2006/0166162 A1* | 7/2006 | Ting | 433/31 |
| 2006/0183072 A1* | 8/2006 | Black | 433/29 |
| 2006/0250796 A1* | 11/2006 | Keller et al. | 362/257 |

FOREIGN PATENT DOCUMENTS

| | | |
|---|---|---|
| DE | 32 33 410 A1 | 4/1984 |
| DE | 297 12 488 U1 | 10/1997 |
| DE | 101 44 414 A1 | 3/2003 |
| DE | 20 2006 014 503 U1 | 1/2007 |
| WO | WO 99/22667 | 5/1999 |

* cited by examiner

*Primary Examiner* — Cris L Rodriguez
*Assistant Examiner* — Edward Moran
(74) *Attorney, Agent, or Firm* — Ann M. Knab; Thad McMurray

(57) ABSTRACT

The invention relates to a light curing device, comprising a light source which is accommodated in a housing which has a light exit, through which light leaves the housing. It is provided that the light exiting direction of the light beam is variable, in particular infinitely variable.

14 Claims, 3 Drawing Sheets

LIGHT CURING DEVICE

CROSS-REFERENCE TO RELATED APPLICATIONS

This application claims foreign priority benefits under 35 U.S.C. §119(a)-(d) from German patent application ser. no. P 10 2007 013 424.1 filed Mar. 20, 2007. In addition, this application claims the benefit under 35 U.S.C. §119(e) of U.S. provisional patent application Ser. No. 60/931,579 filed May 24, 2007.

TECHNICAL FIELD

The invention relates to a light curing device, in particular a light curing device in a substantially stick-like form which is accommodated in a housing which has a light exit, through which light leaves the housing, and wherein the light exiting direction of the light beam is variable, in particular infinitely variable.

BACKGROUND OF THE INVENTION

In the case of such light curing devices, it is known to use optical means, including a reflector and/or a converging lens, to focus the light beam emitted by a light source. Such light curing devices are used for example for the light curing or polymerization of dental materials, the light beam emerging from the light curing device then being directed to the dental restoration part that is to be polymerized.

Dental restoration parts may take a wide variety of forms, and the regions of a tooth that are to be polymerized may be mesial or distal. Especially when they are distal, directing the amount of light required to cure them fully often causes problems. To facilitate this, it has become known to bend away the end of the light guide of the light curing device transmitting the light beam. An example of this is the light curing device known from DE 42 11 230.

Light curing devices of a substantially pistol-like form have proven to be essentially successful, since they make targeted work possible. On the other hand, they are comparatively heavy, in particular if they also hold storage batteries for the power supply.

Furthermore, it has also already been considered to produce stick-like light curing devices in which the light guiding stick is bent away, for example by 45°. In this respect, reference is made for example to DE 101 44 414 A1.

For optimum full curing of the dental restoration part that is to be polymerized, it is important to line up the light exiting direction with the position of the dental restoration part. If, for example, a light curing device with a bent-away light guiding stick, and accordingly a light exiting area extending obliquely in relation to the axis of the light curing device, is held obliquely in relation to the surface of the dental restoration part on the latter, the light energy emitted is typically concentrated only on part of the dental restoration part. This has the effect that the dental restoration part is intensively cured fully on one side, but not on the other side, so that free radicals may remain there.

Although it has been proposed in connection with the detection of decay to use an oblique light exiting area deliberately, in order to promote better decay detection, such a solution is extremely poor for light curing devices.

Furthermore, it has also already become known to fit an attachment onto the end of the light guiding stick and bring about a deflection of the light in this way. In this respect, reference is made to DE 101 24 367 A1.

Furthermore, it is known from DE 32 33 410 A1 to use a light curing device with a flexible light guide, it being possible for the light guide itself to be modified with scissors or a knife or slightly melted with a flame.

This is intended to make the light exit variable. However, a disadvantage here is that, with cut-off light guides, the optical quality is usually poor, especially when inexpensive plastic light guides are used. If the light guide is quite simply cut off obliquely, the light is radiated over a wide angle with low light intensity. Melting also has the effect here that there is only limited focusing, again generally stopping the light emission in the oblique direction.

OBJECTS AND SUMMARY OF THE INVENTION

Against this background, the invention is based on the object of providing a light curing device in a substantially stick-like form which can be easily handled, but is improved with regard to the possibility of full curing even at places that are difficult to access, such as for example in the case of distal dental restoration parts.

According to the invention, it is particularly favorable if a light curing device, such as that provided by the invention, as an element in a substantially stick-like form, permits lateral light exiting without any bent-away portion. This makes introduction into the patients mouth much easier, which is for example relevant especially when treating children, on account of the constricted space in the mouth cavity. Nevertheless, the possibility of controlled focusing and lateral light emission that is infinitely adjustable in its direction, allows even a distal curing location, in other words a distally attached dental restoration part, to be fully cured in a targeted and reliable manner. As a result, it is particularly favorable if a reflection surface which can be adjusted with respect to its angle of obliquity is provided in the stick-like curing device.

It is particularly favorable furthermore if a window which extends arcuately, that is to say covers both the tip of the light curing device and a lateral region near the front end of the stick-like light curing device, is provided.

Here it is also possible to replace the arcuate configuration with a straight or polygonal configuration without impairing the window function. However, it is favorable to give the window substantially a slit-like character, in order to concentrate the light exiting region, it being self-evident that an optical system may also be specifically used in any suitable way to provide the desired focusing effect.

According to the invention, the light exiting area, that is to say the area over which the emitted light beam leaves the light curing device, always includes only part of the window, for example 10%. As a result, it can be ensured that a concentrated radiation is specifically emitted onto the dental restoration part, without fanning out of the beam or scattering of the light occurring.

The adjustability according to the invention of the light exiting angle can also ensure that the emitted light beam falls perpendicularly onto the surface of the dental restoration part. This allows reflections of the surface of the dental restoration part to be avoided as much as possible.

According to the invention, it is particularly favorable that, in spite of the laterally possible light exit, the basic construction of the light curing device in stick form is not impaired. This ensures that ergonomically favorable free rotation is possible. The dentist can bring the luminous area of the emerging light beam specifically into line with the dental restoration part and in this way ensure optimum light curing of the dental restoration part.

In this connection, it is particularly favorable if the adjustability of the light exiting direction is even possible during treatment. For this purpose, the angle of the interior mirror may be adjusted for example by means of a slide, which is attached to the rear end of the light curing device. However, it is also possible to perform the angular adjustment in advance, that is to say before insertion into the patient's mouth, which may be favorable if it is the case that, as far as possible, the adjustment is not to be changed during the treatment.

In addition or as an alternative, a lens that is provided in the light curing device and is part of the optical system may also be displaced. With appropriate focusing of the lens, this also allows an angular adjustment of the emerging light beam to be accomplished, or else the fanning out of the beam to be adapted broadly to the requirements.

According to the invention, it is particularly favorable if a light-emitting diode in the form of a single LED chip is arranged in the stick-like light curing device—at a distance from the front end—and the light radiation emitted to be directed to the front end of the light curing device by means of a reflector, which at least partially surrounds the LED chip. A combination of such a reflector, for example a parabolic reflector, with a converging lens has a particularly favorable focusing effect for the light radiation emitted, it being self-evident that, as far as possible, the reflector reflects at least almost 100% of the light radiation emitted. The converging lens or the converging lenses of the optical system are transmissive for the emitted wavelength range.

If, on the other hand, the reflector is transmissive to the long-wave radiation emitted, for example in the infrared range, a smaller proportion of infrared radiation is directed forward. This configuration is favorable if combined heat and light curing is not desired, but exclusively light curing. Especially in the case of this solution, adequate cooling of the LED chip must be ensured; for this purpose, a quite large heat capacitance element may be used, provided in the grip of the light curing device.

According to the invention, it is also particularly favorable that the mirror which forms the reflection surface according to the invention can be kept very light, for example lighter than a prismatic element with which light deflection could also be accomplished. This ensures that the front end of the stick-like light curing device can be made particularly lightweight.

With an appropriately closed formation of the housing of the light curing device according to the invention, the light curing device is easy to clean and, if required, can even be sterilized. For example, the material that forms the window at the front end of the light curing device may also provide a protective enclosure which surrounds and covers over the entire light curing device, or at least a substantial part of the light curing device.

Sleek surfaces, with the front end of the housing of the light curing device rounded on all sides, which to this extent substantially has the form of a cigar, prevent contaminants from remaining on the housing, and ensure a construction that fits well into the mouth.

In a further advantageous configuration, it is provided that the window extends arcuately over the front end of the light curing device, and in particular covers an arc angle of more than 60°, with preference more than 90° and with particular preference more than 120°.

In a further advantageous configuration, it is provided that, at least over its front half, the light curing device has sleek surfaces and can be cleaned and/or sterilized in particular by immersion in a cleaning liquid or sterilizing liquid, at least over more than half of its length, in particular over more than 90% of its length.

In a further advantageous configuration, it is provided that, in at least one position, the reflection surface extends obliquely away from the housing of the light curing device, and that the angle of obliquity is adjustable.

In a further advantageous configuration, it is provided that the lens, which is adjustable in particular in its axial position, is arranged between the reflection surface and the light source, and that the focus of the light curing device is adjustable by means of the lens formed as a converging lens.

In a further advantageous configuration, it is provided that the light exit takes place through a window, the relative position of which is fixed in relation to the light source.

In a further advantageous configuration, it is provided that the light beam can be diverted from a longitudinal axis of the light curing device by means of a reflection surface.

In a further advantageous configuration, it is provided that the reflection surface is adjustable in relation to the light curing device.

In a further advantageous configuration, it is provided that the light curing device has at least one lens, by which the light cone of the light beam can be influenced.

In a further advantageous configuration, it is provided that the lens is adjustable in its alignment, in particular in its axial alignment.

In a further advantageous configuration, it is provided that the light curing device has a housing, which is of a closed form in the region of the lens and/or the reflection surface.

In a further advantageous configuration, it is provided that an adjustment of the lens and/or of the reflection surface is performed by an adjusting device through a housing wall.

In a further advantageous configuration, it is provided that a window is arranged in the end region of the light curing device on the light exiting side and extends in particular parallel to the longitudinal axis of the light curing device, and in particular also laterally in relation to the latter.

In a further advantageous configuration, it is provided that the window is formed from glass or plastic or a film.

In a further advantageous configuration, it is provided that the reflection surface is mounted on at least one pivot bearing, which can be fastened to the housing, and that the reflection surface is adjustable over angle of at least 10°, in particular approximately 45°.

In a further advantageous configuration, it is provided that the reflection surface is of a planar or concave form.

In a further advantageous configuration, it is provided that the reflection surface is deformable.

In a further advantageous configuration, it is provided that the reflection surface is part of a reflection element which is connected to the housing in a fixed manner or by means of a hinge, in particular a film hinge.

In a further advantageous configuration, it is provided that a reflector is arranged adjacent the light source.

Other advantages, details and features are provided by the following description of an exemplary embodiment of the invention on the basis of the drawings, in which:

DETAILED DESCRIPTION

Figure 1:
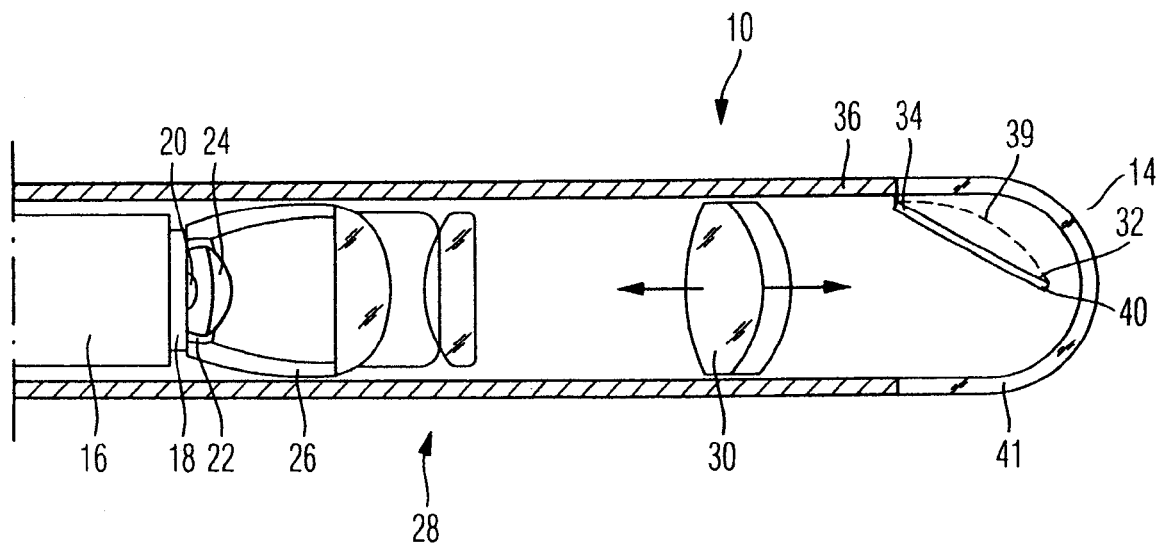
FIG. 1 shows a cut-open view of the front part of one embodiment of a light curing device according to the invention.

The light curing device 10 schematically represented in FIG. 1 has a housing 12. The housing 12 is substantially longitudinally cylindrical and has at its front end a hemispherical window 14. The rear region is not represented; there, the cylindrical form is continued, so that the housing 12 is substantially given the form of a stick or pen and can be held in the hand in the manner of a pencil. It is particularly preferred, however, that a triggering button (not represented) is provided on the upper side of the stick-like light curing device 10, and can then be actuated by the dentist's index finger, so that the stick-like light curing device can be held like a pointing element and is grasped with the hand above.

An energy supply is accommodated in the rear end of the housing 12, which is not represented in the figures, either a quite compact storage battery being provided or, if required, a power supply cable that runs to a base station.

The housing 12 also has in its rear end a heat storage element 16, which consists for example of copper and serves for the intermediate storage of the heat emitted. It is preferred in this connection that heat can be dissipated well when the rear end of the light curing device 10 is inserted in a base station.

The heat storage element 16 is in thermally conducting connection with a base element 18 of the LED chip 20. The LED chip 20 is surrounded by a reflector 22, which reflects the emitted light beam forward, that is to say toward the front end 14. The reflector 22 is closed off at its front end by a converging lens 24, which focuses the light emitted.

The converging lens 24 is also surrounded by a second reflector 26, which for its part is closed off by converging lens optics 28, which further focus and parallelize the light radiation emitted. For this purpose, in the exemplary embodiment represented, the combination of a piano-convex lens, a double concave lens and a further plano-convex lens is provided, as known per se.

According to the invention, it is envisaged to provide an adjustable lens 30 in the path of rays behind the converging lens optics 28. The adjustability relates here at least to the axial adjustability, that is to say the adjustability in the direction of the optical axis of the emitted light beam. In the case of a non-circular configuration of the lens 30, however, a rotational adjustability can also be accomplished, in order to divert the light beam in the desired way.

According to the invention, a reflection surface 32 is provided in the light beam behind the lens 30. The reflection surface 32 extends from a first end 34, which is adjacent the wall 36 of the housing 12, obliquely downward. In the position represented, the front end 40 of the reflection surface 32 ends approximately in the optical axis of the light curing device 10.

The reflection surface 32 has an adequate width, so that the emitted light beam is completely reflected there. The width is to this extent greater than the light spot occurring there, to be precise even in the least focusing position of the lens 30.

According to the invention, the reflection surface 32 is adjustable in its angle of inclination. The adjustment takes place about the upper rear end 34. There, either a joint with a joint pin is provided, or the reflection surface 32 is attached there in the manner of a film hinge and is movable.

According to the invention, it is envisaged to adapt the adjustment of the reflection surface 32 to the requirements. For example, the concave form 39, represented by dashed lines, of the reflection surface is also desired, in order to achieve focusing. For this purpose, the reflection surface 34 is expediently rather clamped in a fixed manner at its end 34, so that the concave form is automatically obtained when the end 40 is moved downward.

The emerging light beam is outwardly guided by a window 41, as can be seen from the further figures.

The pivotability of the reflection surface 32 allows the emitted light beam to be reflected in accordance with the known equation, angle of incidence=angle of reflection. This is represented in the further FIGS. 3 and 4, in which—as also in FIG. 5—the same designations indicate the same parts.

Figure 2:
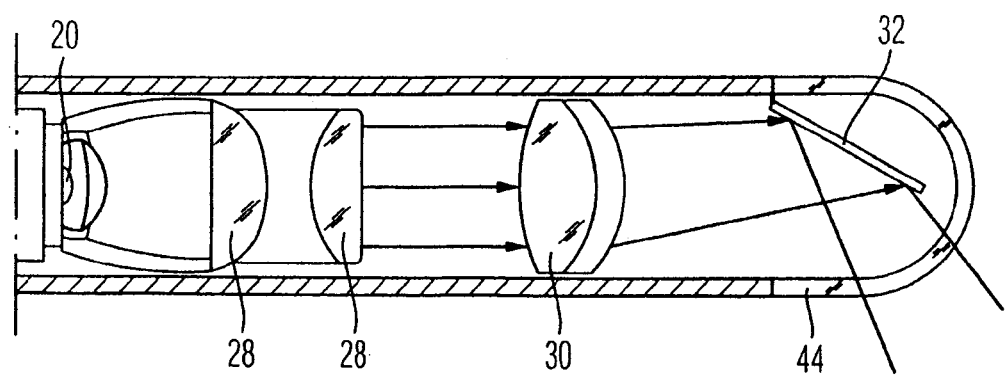
FIG. 2 shows the embodiment according to FIG. 1 with the light beam represented.

FIG. 2 shows a position of the lens 30 quite far forward. In this position, less strong focusing takes place, so that the radiation emitted is intended for the full curing of a quite large dental restoration part.

Figure 3:
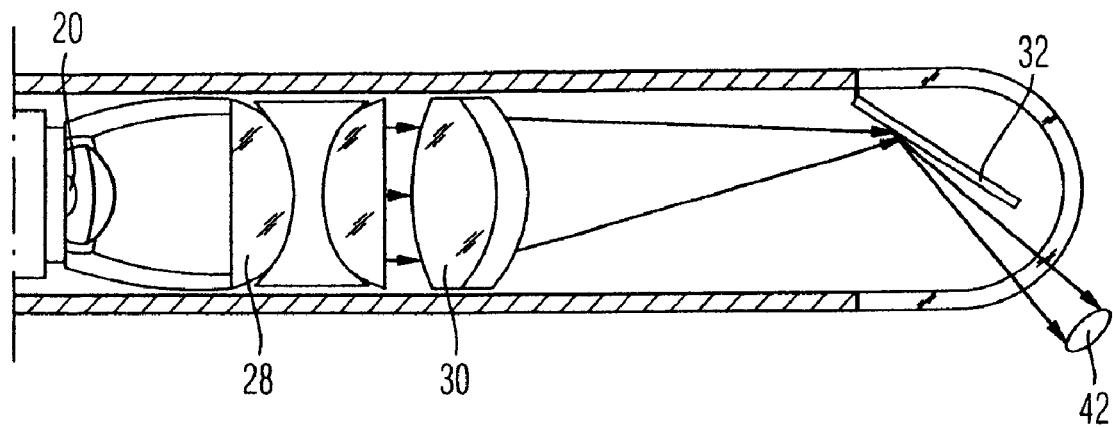
FIG. 3 shows the embodiment according to FIG. 1 in a further position of the lens.

By contrast, FIG. 3 shows the same position of the reflection surface 32, but a position of the lens 30 that brings about strong focusing. For this purpose, the lens 30 is closer to the converging lens optics 28. The light area 42 impinged in this way is quite small, so that this position is suitable for the full curing of a quite small dental restoration part.

Figure 4:
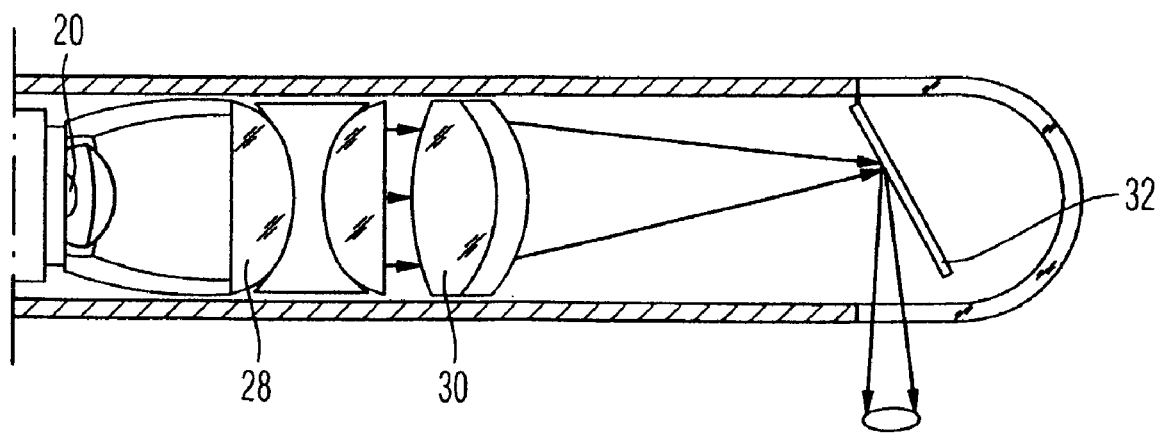
FIG. 4 shows the embodiment according to FIG. 1 in another position of the reflection surface.

FIG. 4 shows by contrast the same position of the lens 30, but a more lowered position of the reflection surface 32. In this position, the incident light is diverted laterally at an angle of approximately 90°, so that this position is particularly suitable for distal dental restoration parts. The light yield is nevertheless no less than in the case of the positions according to FIGS. 2 and 3.

Figure 5:
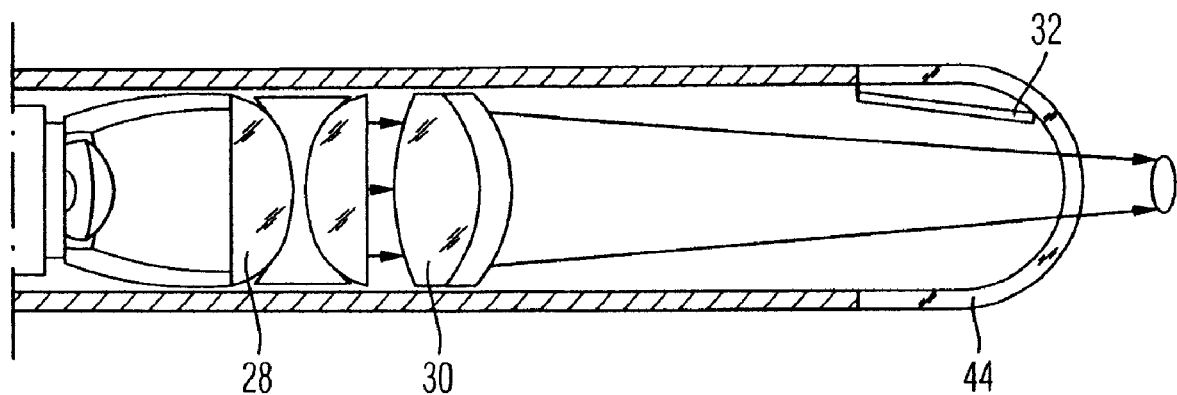
FIG. 5 shows the embodiment according to FIG. 1 in a further position of the reflection surface.

FIG. 5 shows by contrast a position of the reflection surface 32 in which it has been completely raised upward, the lens 30 being positioned into the rearmost position, that is to say adjacent the converging lens optics 28. In this position, the reflection surface 32 is not impinged with light radiation; rather, the light radiation emitted exits forward from the housing 12 in the optical axis, in order to bring about light curing there. For adjustment both of the reflection surface 32 and of the lens 30, means known per se are provided, even if this is not represented in the figures. For example, it is possible to ensure the desired angular adjustment by means of corresponding slides or levers, which act for example on the front end 40 of the reflection surface 32 and on the lens 30 at two places that are against and opposite each other. These levers or slides end at the rear end (not represented) of the housing 12 and can be manually actuated quite well. Alternatively, it is also possible to ensure a sliding adjustment through the wall 36 of the housing 12 by means of a magnetic coupling.

The housing 12 is in any event completely closed, at least in the region represented in the figures. To allow light to pass through, a window 44 is accordingly provided at the front end 14 of the light curing device 10. The window 44 is substantially of a slit-like form, so that it does not impair the light exit there, but is not accompanied by any significant mechanical weakening of the housing 12. In the exemplary embodiment represented of the hemispherical end 14, it extends such that it follows the hemisphere into the cylindrical region of the housing 12. The window 44 is asymmetric, so that for example it ends at the top in a 45° position of the hemispherical end 14, but at the bottom extends over the entire hemispherical end, and for example a few millimeters beyond this end to the rear. This means that the window 44 allows light to exit both upward and to the side on one side, corresponding to the position of the reflection surface 32. The choice of the lateral dimensions, that is to say the width of the window, is chosen such that no shading is possible, even if the lens 30 is in the position according to FIG. 2.

According to the invention, the window 44 is closed, a transparent plastic being provided there. The plastic 44 may either take the form of a plastic insert, or with preference a thin plastic enclosure, which then encloses the entire housing 12 and to that extent is also liquid-impermeable.

The reflection surface 32 may be formed in any desired suitable way. It is particularly advantageous if a thin plastic element that is made reflective by vapor-depositing or coating is used. It is particularly favorable in this connection that the inside of the light curing device is hermetically sealed from the outside, so that no dust deposits reduce the light yield. With a gastight formation of the light curing device according to the invention, which can then be filled with pure nitrogen for example, the possibility of any instances of corrosion and material degradation caused by gases present in the ambient air can also be eliminated.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A light curing device (10), comprising a light source (20) which is accommodated in a stick-like compact handheld housing comprising a cylindrical portion (36) which terminates in a hemispherical end (14) and which has a light exit in the form of an arcuate window (44) of a substantially slit-like form through which light in the form of a light beam leaves the housing, the window (44) extending parallel to the longitudinal axis of the light curing device (10), and also laterally in relation to the latter, an adjustable position lens (30) and a variable position reflective surface (32) being mounted in the housing, and wherein the direction of the light beam is continuously variable by movement of the adjustable position lens (30) and/or the variable position reflective surface (32), whereby the light beam may exit through the window either straight forward or at right angles to the cylindrical portion, respectively, wherein the arcuate window (44) extends over an angle greater than 120°, the arcuate window (44) is asymmetrical and extends upwards to a top of the window at a 45° position and extends to a bottom of the window over the entire hemispherical end and a few millimeters beyond the hemispherical end towards the rear of the device so that light may exit upwardly as well as straight forward and at a right angle.

2. The light curing device as claimed in claim 1, wherein the light beam can be diverted to one side of a longitudinal axis of the light curing device (10) by the reflection surface (32).

3. The light curing device as claimed in claim 1, wherein the light curing device has a further lens (28), by which the light beam can be influenced.

4. The light curing device as claimed in claim 3, wherein the lens (30) is adjustable in its axial alignment.

5. The light curing device as claimed in claim 3, wherein the housing is of a closed form in the region of the lens (28, 30) and/or the reflection surface (32).

6. The light curing device as claimed in claim 3, wherein an adjustment of the lens is performed by an adjusting device through a housing wall.

7. The light curing device as claimed in claim 1, wherein the window (44) is formed from one of glass or plastic or a film.

8. The light curing device as claimed in claim 2, wherein the reflection surface (32) is mounted on at least one pivot bearing, which is fastened to the housing, and wherein the reflection surface (32) is adjustable over an angle to approximately 45 degrees.

9. The light curing device as claimed in claim 2, wherein the reflection surface is of either a planar or concave form.

10. The light curing device as claimed in claim 2, wherein the reflection surface is deformable.

11. The light curing device as claimed in claim 2, wherein the reflection surface is part of a reflection element which is either connected to the housing in a fixed manner or by a hinge.

12. The light curing device as claimed in claim 1, wherein a reflector (22) is arranged adjacent the light source.

13. The light curing device as claimed in claim 2, wherein an adjustment of the reflection surface (32) is performed by an adjusting device through a housing wall.

14. The light curing device as claimed in claim 11 wherein the hinge is a film hinge.

* * * * *

UNITED STATES PATENT AND TRADEMARK OFFICE
CERTIFICATE OF CORRECTION

| | | |
|---|---|---|
| PATENT NO. | : 8,382,472 B2 | Page 1 of 1 |
| APPLICATION NO. | : 12/077721 | |
| DATED | : February 26, 2013 | |
| INVENTOR(S) | : Plank et al. | |

It is certified that error appears in the above-identified patent and that said Letters Patent is hereby corrected as shown below:

Title page, item (60) should read:

--(60) Related U.S. Application Data
Provisional application No. 60/931,579, filed on May 24, 2007.--

Signed and Sealed this
Seventeenth Day of September, 2013

Teresa Stanek Rea
*Deputy Director of the UnitedStates Patent and Trademark Office*